United States Patent [19]
Bedeschi et al.

[11] Patent Number: 6,093,721
[45] Date of Patent: Jul. 25, 2000

[54] AMIDINO-CAMPTOTHECIN DERIVATIVES

[75] Inventors: Angelo Bedeschi, Milan; Walter Cabri, Rozzano; Ilaria Candiani, Busto Arsizio; Laura Capolongo, Milan, all of Italy

[73] Assignee: Pharmacia & Upjohn S.p.A., Milan, Italy

[21] Appl. No.: 09/269,177

[22] PCT Filed: Jul. 20, 1998

[86] PCT No.: PCT/EP98/04919

§ 371 Date: May 13, 1999

§ 102(e) Date: May 13, 1999

[87] PCT Pub. No.: WO99/05103

PCT Pub. Date: Feb. 4, 1999

[30] Foreign Application Priority Data

Jul. 25, 1997 [GB] United Kingdom .................... 9715821

[51] Int. Cl.[7] .......................... C07D 491/22; A61K 31/47
[52] U.S. Cl. ............................................... 514/283; 546/48
[58] Field of Search ................................. 546/48; 514/283

[56] References Cited

U.S. PATENT DOCUMENTS 5,602,141  2/1997  Bedeschi et al. ....................... 514/279
5,614,628  3/1997  Cabri et al. ................................ 546/48
5,840,899  11/1998  Bedeschi et al. ......................... 546/48

FOREIGN PATENT DOCUMENTS

WO 95/22549  8/1995  WIPO .

OTHER PUBLICATIONS

Bedeschi et al. (Bioorganic & Medicinal Chemistry Letters, vol. 6, No. 6, pp. 671–674 (1996).

*Primary Examiner*—Richard L. Raymond
*Assistant Examiner*—Bruck Kifle
*Attorney, Agent, or Firm*—Oblon, Spivak, McClelland, Maier & Neustadt, P.C.

[57] ABSTRACT

A water soluble camptothecin derivative which is 20(S)-7-ethyl-9(N-methyl-N-phenyl)amidino-camptothecin and pharmaceutically acceptable salts thereof, pharmaceutical compositions containing them and a process for their preparation are described. The compound of the invention and its pharmaceutically acceptable salts are useful antitumor agents and are further charactcrised by having a remarkable therapeutic index.

11 Claims, No Drawings

AMIDINO-CAMPTOTHECIN DERIVATIVES

The present invention relates to amidino-camptothecin derivatives and, more particularly, it relates to 20(S)-7-ethyl-9-(N-methyl-N-phenyl) amidino-camptothecin and its pharmaceutically acceptable salts, to a process for their preparation and to pharmaceutical compositions comprising them.

Camptothecin and some of its analogous compounds such as, for instance, 9-amino-camptothecin, display potent antitumor activity by inhibiting topoisomerase I which is a monomeric enzyme involved in some important cellular functions and cells growth. For a general reference to camptothecin and its derivatives see, for instance, Wani et al., J. Med. Chem. 1987, 30, 1774; Hsiang et al., Cancer Res. 1989, 49, 4385 and Cancer res. 1989, 49, 1465. Our previous international patent application No. WO 95/22549 describes water-soluble camptothecin derivatives of formula

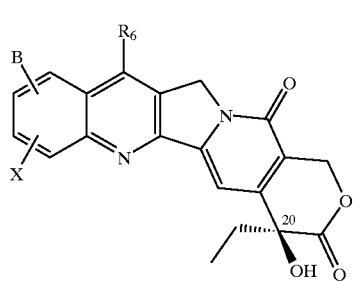

(I)

wherein
B is a group B' or B"

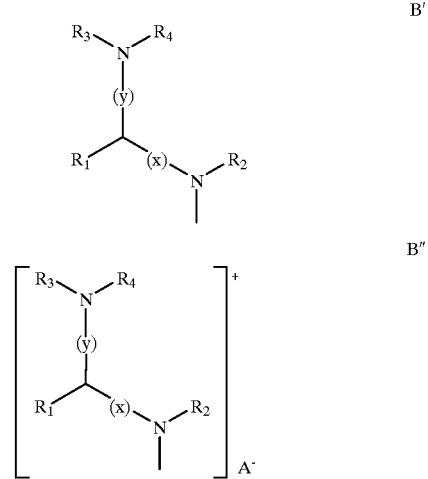

wherein
each of (x) and (y) is a single or double bond;

$R_1$ and $R_2$ are, each independently, hydrogen, $C_1$–$C_6$ alkyl, $C_3$–$C_7$ cycloalkyl, phenyl $C_1$–$C_6$ alkyl or an optionally substituted phenyl ring;

$R_3$ and $R_4$ are
(a) each independently substituents having the same meaning of $R_1$ and $R_2$ or
(b) combined together with the nitrogen atom to which they are linked to form a 3–7 membered saturated optionally substituted heteromonocyclic ring, which may additionally contain another heteroatom selected among nitrogen, oxygen and sulphur; and $A^-$ is a pharmaceutically acceptable anion of a pharmaceutically acceptable inorganic or organic acid; provided that, (i) when (x) is a double bond, (y) is a single bond and when (y) is a double bond, (x) is a single bond, and
(ii) when B is a group B', then one of $R_2$, $R_3$ and $R_4$ is absent;

$R_6$ is hydrogen or a $C_1$–$C_6$ alkyl; and
X is hydrogen, $C_1$–$C_6$ alkyl, $C_1$–$C_6$ alkoxy, $C_1$–$C_6$ acyloxy, $C_3$–$C_7$ cycloalkyl, $C_3$–$C_7$ cycloalkoxy, benzoyloxy, amino, hydroxy, nitro, a halogen atom or a methylenedioxy group linked to the positions 10 and 11 of the molecule.

The compounds therein described as well as the natural occurring camptothecin have a 20(S)-configuration. As set forth in the above reported formula (I), a dotted line (⁙⁙⁙) in position 20 indicates a substituent in the α-configuration, i.e. below the plane of the ring, whereas a wedged line (◂) indicates a substituent in the β-configuration, i.e. above the plane of the ring.

The compounds of formula (I) therein described are inhibitors of topoisomerase I and are thus effective in therapy as antitumor agents, for instance against leukaemia or other solid tumours such as colon and rectal tumours.

Because of their water-solubility, the compounds of formula (I) result to be extremely useful for preparing pharmaceutical formulations suitable, in particular, of being administered in aqueous media.

Besides being biologically active and endowed with chemico-physical characteristics which render them particularly advantageous (e.g. water-solubility) other parameters, mainly related to toxicity, result to be important when referring to the administration of drugs.

To this extent, it is worth noting that the use of a drug in therapy is significantly influenced by its therapeutic index (T.I.) value, as a lethal dose/effective dose ratio ($DL_{10}/DE_{50}$), which often results to be a limiting factor.

Accordingly, it is an object of the present invention to provide compounds which, while displaying potent antitumor activity and excellent water-solubility, are also endowed with a favourable, i.e. high therapeutic index.

This is even more appreciated when referring, in particular, to drugs which have to be administered according to a prolonged schedule treatment.

It has now been surprisingly found that within the class of camptothecin derivatives of formula (I) described in the aforementioned application WO 95/22549, the compound 20(S)-7-ethyl-9-(N-methyl-N-phenyl)amidino-camptothecin (internal code PNU 166300) and its pharmaceutically acceptable salts, being not specifically disclosed therein, are characterised by a therapeutic index value particularly high.

Therefore, it is the object of the present invention the compound 20(S)-7-ethyl-9-(N-methyl-N-phenyl)amidino-camptothecin and its pharmaceutically acceptable salts.

In the present description, unless otherwise specified, with the term pharmaceutically acceptable salts we intend the salts of 20(S)-7-ethyl-9-(N-methyl-N-phenyl)amidino-camptothecin with pharmaceutically acceptable organic or inorganic acids such as, for instance, citric, fumaric, maleic, malic, tartaric, benzoic, acetic, phenylacetic, methanesulphonic, ethanesulphonic, benzenesulphonic, p-toluenesulphonic, hydrochloric, hydrobromic, sulphuric, phosphoric, diphosphoric or nitric acid.

These novel water-soluble derivatives, while maintaining an antitumor activity essentially comparable to that of the corresponding compounds of formula (I), result to possess a significantly higher therapeutic index.

The compound of the present invention and its related salts may be prepared according to a process comprising reacting 20(S)-9-amino-7-ethyl-camptothecin of formula with a compound of formula

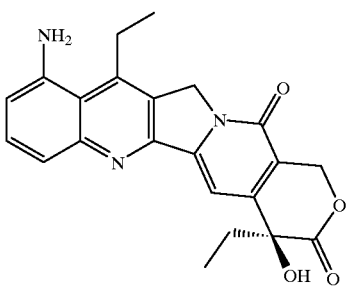

(II)

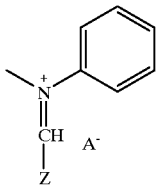

(III)

wherein A⁻ is either a pharmaceutically acceptable anion as defined above or any other suitable anion and Z is a leaving group such as, for instance, $C_1$–$C_6$ alkoxy, $C_3$–$C_7$ cycloalkoxy, $C_1$–$C_6$ acyloxy, benzoyloxy, $C_3$–$C_7$ cycloacyloxy, a halogen atom, trifluoromethanesulphonyloxy, p-toluenesulphonyloxy or methanesulphonyloxy and, if desired, converting the thus obtained 20(S)-7-ethyl-9-(N-methyl-N-phenyl)amidino-camptothecin into a pharmaceutically acceptable salt.

Preferably, Z is methoxy, ethoxy, propoxy, isopropoxy, acetoxy, benzoyloxy, fluorine, chlorine, bromine, iodine, trifluoromethanesulphonyloxy, p-toluenesulphonyloxy or methanesulphonyloxy.

The process for the preparation of 20(S)-7-ethyl-9-(N-methyl-N-phenyl)amidino-camptothecin is carried out by reacting 20(S)-9-amino-7-ethyl-camptothecin or formula (II), dissolved in a suitable solvent as defined below, with from a stoichiometric amount to a large excess of a compound of formula (III), at a temperature of from about –20° C. to about 100° C., preferably within the range of 0°–λ° C. for a period varying from few minutes to several days, preferably from about one hour to one day, optionally in the presence of a suitable inorganic or organic base.

Suitable solvents include water, dimethylformamide (DMF), methanol, acetic acid, chloroform, dioxane, tetrahydrofuran and mixtures thereof.

Suitable inorganic bases may be alkali or alkaline earth metals hydroxides, carbonate or bicarbonate such as, for instance, NaOH, $NaHCO_3$, $Na_2CO_3$ or $CaCO_3$. Suitable organic bases may be, e.g., trialkylamines such as triethylamine or diisopropylethylamine or heteroaromatic bases such as pyridine and optionally substituted pyridines (e.g. 2,6-lutidine).

The compounds of formula (II) and (III), as starting materials, are known compounds or may be obtained according to conventional methods.

For a reference to 9-amino-7-ethyl-camptothecin of formula (II) and its preparation see, for instance, the aforementioned Wani et al., J. Med. Chem. 1986, 29, 2358.

The starting 9-amino-7-ethyl-camptothecin has a 20(S)-configuration corresponding to the configuration of the natural occurring camptothecin. Said configuration is retained throughout the process for preparing 7-ethyl-9-(N-methyl-N-phenyl)amidino-camptothecin.

The antitumor activity of the compound object of the present invention was shown, for example, by evaluating the "in vivo" antileukaemic activity [see method (a) below].

7-Ethyl-9-N,N-dimethylamidino-camptothecin and 9-(N-methyl-N-phenyl)amidino-camptothecin, hereinafter referred to as reference compounds having internal codes PNU 157560 and PNU 157558, respectively, being both structurally close to the compound of the invention, have been chosen as comparison compounds.

To this extent, it is worth noting that although included within the general formula (I) of WO 95/22549 but not specifically exemplified therein, both PNU 157560 and PNU 157558 were described by A. Bedeschi et al. in Bioorg. & Med. Chem. letters, No 6, 671–674, 1996, and therein referred to as compounds (5g) and (5d), respectively.

Topotecan, a widely known camptothecin derivative markedly available as antitumor agent, was herewith selected as a further reference compound.

For a general reference to topotecan see, for instance, A. Tanizawa et al., J. Natl. Cancer Inst. 1994, 86, 836–842.

While maintaining comparable biological activity with respect to the reference compounds, 20(S)-7-ethyl-9-(N-methyl-N-phenyl)amidino-camptothecin resulted to possess a significantly higher therapeutic index.

The therapeutic index (T.I.) was calculated by using a computer program (Finney D. J.—PROBIT ANALYSIS, London 1964) as a lethal dose/effective dose ratio ($DL_{10}$/$DE_{50}$) wherein, $DL_{10}$ is the dose inducing 10% of death in healthy mice treated with the tested compounds and $DE_{,50}$ is the dose inducing a 50% increase of survival in mice treated with the tested compounds in comparison to the untreated controls, both groups bearing L1210 leukaemia.

Method (a): evaluation of antitumor activity

The "in vivo" antitumor activity was evaluated against L1210 murine leukaemia. At day 0, iv inocula of $10^5$ cells in CDF1 female mice were performed. The treatment schedule consisted of a single iv injection at day+1.

As reported in the following table 1, the compound of the invention resulted to be endowed with an "in vitro" antitumor activity essentially comparable to that of PNU 20 157560, PNU 157558 and topotecan.

In addition, it resulted to be unexpectedly endowed with a therapeutic index significantly higher than that of the whole group of reference compounds.

Table 1

"In vivo" L1210 antileukaemic activity expressed in terms of percent increase in median survival time at the optimal dose (O.D.) in comparison with untreated controls (%T/C) and therapeutic index (T.I.) of 20(S)-7-ethyl-9-(N-methyl-N-phenyl)amidino-camptothecin (PNU 166300) and of the reference compounds PNU 157560, PNU 157558 and topotecan.

| COMPOUNDS | IN VIVO ACTIVITY - L1210 (iv, iv + 1) | | T.I. ($DL_{10}$/$DE_{50}$) |
|---|---|---|---|
| | dose (mg/kg) | % T/C | |
| PNU 166300 (compound of the invention) | 15 | 200 | 4 |
| | 22.5 | 212 | |
| PNU 157560 | 15 | 193 | 1.9 |
| PNU 157558 | 15 | 157 | 1.9 |

-continued

| COMPOUNDS | IN VIVO ACTIVITY - L1210 (iv, iv + 1) | | T.I. ($DL_{10}/DE_{50}$) |
|---|---|---|---|
| | dose (mg/kg) | % T/C | |
| Topotecan | 15 | 172 | 1.3 |

The compounds of the invention can be administered in a variety of dosage forms, e.g. orally, in the form of tablets, capsules, lozenges, liquid solutions or suspensions; rectally, in the form of suppositories; parenterally, e.g. intramuscularly, intravenously, intradermally or subcutaneously; or topically.

The dosage depends upon the age and the conditions of the patient, the administration route and the stage of the disease.

Specific dosage regimens may be fit to any particular subject on the basis of the individual need and the professional judgement of the person administering or supervising the administration of the drug. Average dosages adopted for the administration to adults humans may range from 0.1 to 60 mg of camptothecin derivative per kg of body weight; a particularly preferred range may be from 1 to 40 mg of camptothecin derivative per kg of body weight divided into a single dose or into more daily doses.

Pharmaceutical compositions containing 20(S)-7-ethyl-9-(N-methyl-N-phenyl)amidino-camptothecin or its pharmaceutically acceptable salts, as an active ingredient, in association with a pharmaceutically acceptable carrier and/or diluent are also within the scope of the present invention.

These pharmaceutical compositions contain an amount of active ingredient which is therapeutically effective to display antileukaemic and/or antitumor activity.

As a part of the pharmaceutical compositions according to the present invention, pharmaceutically acceptable binding agents and/or adjuvant materials may also be included.

The active ingredient may also be mixed with other active principles which do not impair the desired action and/car supplement the desired action.

The pharmaceutical compositions containing 20(S)-7-ethyl-9-(N-methyl-N-phenyl)amidino-camptothecin or related salts are usually prepared according to conventional methods and may be administered in a pharmaceutical suitable form as described, for instance, in the aforementioned international application No. WO 95/22549.

With the aim of better illustrating the present invention without limiting it the following examples are now given.

EXAMPLE 1

Preparation of 20(S)-7-ethyl-9-(N-methyl-N-phenyl) amidino-camptothecin hydrochloride A solution of oxalyl chloride (2.25 ml) in 15 ml of $Et_2O$ (anhydrous) was dropped into a solution of N-methylformanilide (3.1 ml) in 35 ml of $Et_2O$ (anhydrous) cooled to −30° C. After the addition the cooling bath was removed and the reaction mixture was left at r.t. for 2.5 hr. Toluene (35 ml) was added and the solvents were evaporated almost completely at reduced pressure (60° C.). The residue was dissolved in $CH_2Cl_2$ (anhydrous, 17 ml), then about ⅔ of this solution were added to a suspension of 7-ethyl-9-amino-20(S)-camptothecin (0.25 g) in $CH_2Cl_2$ (20 ml) and N-methylformanilide (17 ml). At the end of the dropping the reaction was poured into $H_2O$ (50 ml), $CH_2Cl_2$ (70 ml) was added therein and the pH was brought to 6.2 with NaOH 2N. The organic phase was dried with $Na_2SO_4$, evaporated and purified by flash chromatography to give 0.220 g of 20(S)-7-Ethyl-9-(N-methyl-N-phenyl)amidino-camptothecin (67.6G yield).

$^1$H NMR 200 MHz (DMSO-$d_6$) d (ppm): 0.87 (t, J=7.2 Hz, 3H), 1.29 (t, J=7.5 Hz, 3H), 1.85 (m, 2H), 3.55 (s, 3H), 3.57 (m, 2H), 5.26 (s, 2H), 5.42 (s, 2H), 6.48 (s, 1H), 7.08 (dd, J=1.3, 7.2 Hz, 1H) 7.18–7.40 (m, 5H), 7.28 (s, 1H) 7.64 (dd, J=7.2, 8.3 Hz, 1H), 7.80 (dd, J =1.3, 8.3 Hz, 1H), 8.26 (s, 1H).

MS (EI; source temperature 225°): m/z 508(2, (M)$^-$°); 464 (3, (M-$CO_2$)$^{+°}$); 402 (6, (M-$PhNCH_3$)$^-$; 358 (12, (M-$CO_2$-$PhNCH_3$)); 107 (100, ($PhNCH_3$)$^{+°}$; 106 (21, ($PhNCH_3$)$^+$.

EXAMPLE 2

Lyophilised formulation of 20(S)-7-ethyl-9-(N-methyl-N-phenyl)amidino-camptothecin hydrochloride A pharmaceutical lyophilised formulation was manufactured by dissolving 0.22 g of the title compound into a mixture of 100 ml of $H_2O$, 20 ml of $CH_3CN$ and 4 ml of HCl 2N. The solution was lyophilised for 72 hr to give 0.230 g of the lyophilised pharmaceutical formulation.

What is claimed is:

1. A compound which is 20(S)-7-ethyl-9-(N-methyl-N-phenyl)amidino-camptothecin or a pharmaceutically acceptable salt thereof.

2. A compound according to claim 1 in the form of hydrochloride salt.

3. A process for the preparation of a compound according to claim 1 comprising reacting 20(S)-9-amino-7-ethyl-camptothecin with a compound of formula

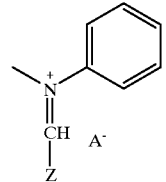

(III)

wherein A is a pharmaceutically acceptable anion or any other suitable anion and Z is a leaving group selected from the group consisting of $C_1$–$C_6$ alkoxy, $C_3$–$C_7$ cycloalkoxy, $C_1$–$C_6$ acyloxy, benzoyloxy, $C_3$–$C_7$ cycloacyloxy, a halogen atom, trifluoromethanesulphonyloxy, p-toluenesulphonyloxy or methanesulphonyloxy and, if desired, converting the thus obtained 20(S)-7-ethyl-9-(N-methyl-N-phenyl)amidino-camptothecin into a pharmaceutically acceptable salt.

4. A process according to claim 3 wherein A$^-$ is an anion of a pharmaceutically acceptable organic or inorganic acid selected from the group consisting of citric, fumaric, maleic, malic, tartaric, benzoic, acetic, phenylacetic, methanesulphonic, ethanesulphonic, benzenesulphonic, p-toluenesulphonic, hydrochloric, hydrobromic, sulphuric, phosphoric, diphosphoric or nitric acid.

5. A pharmaceutical composition comprising, as an active principle, a therapeutically effective amount of a compound as defined in claim 1 in admixture with a pharmaceutically acceptable diluent and/or carrier.

6. A method of treating tumors, comprising administering the compound of claim 1 to a patient in need thereof.

7. The method of claim 6, wherein the patient is a human.

8. The method of claim 7, wherein 0.1 to 60 mg of the compound per kg of weight is administered to the patient per dose.

9. The method of claim 7, wherein 1 to 40 mg of the compound per kg of weight is administered to the patient per dose.

10. The method of claim 6, wherein the compound is administered orally, intramuscularly, intraveneously, intradermally, subcutaneously, rectally or topically.

11. The method of claim 6, wherein the compound is administered in the form of a tablet, capsule, lozenge, liquid solution or suspension or suppository.

* * * * *